United States Patent
Brusseaux et al.

[11] Patent Number: 6,104,299
[45] Date of Patent: Aug. 15, 2000

[54] DEVICE FOR MONITORING POLLUTION CAUSED BY MOTOR VEHICLES IN AN URBAN AREA

[75] Inventors: Thierry Brusseaux, Avenay; Xavier Flinois, Paris, both of France

[73] Assignee: Schlumberger systemes, Montrouge, France

[21] Appl. No.: 09/319,990

[22] PCT Filed: Jan. 7, 1998

[86] PCT No.: PCT/FR98/00022

§ 371 Date: Jun. 15, 1999

§ 102(e) Date: Jun. 15, 1999

[87] PCT Pub. No.: WO98/30990

PCT Pub. Date: Jul. 16, 1998

[30] Foreign Application Priority Data

Sep. 1, 1997 [FR] France .................................. 97 00237

[51] Int. Cl.[7] .................................. G08B 21/00
[52] U.S. Cl. .................. 340/603; 340/632; 340/928; 340/932.2; 73/23.38; 73/23.41; 73/31.02; 194/205; 194/212
[58] Field of Search ............ 340/603, 438, 340/632, 932.2, 928, 905; 194/205, 217, 318, 902, 212; 73/1.06, 23.32, 23.38, 23.41, 31.01, 31.02

[56] References Cited

U.S. PATENT DOCUMENTS

| | | | |
|---|---|---|---|
| 4,526,028 | 7/1985 | Hubner | 73/23 |
| 4,943,929 | 7/1990 | Simonoff | 364/496 |
| 5,276,434 | 1/1994 | Brooks et al. | 340/632 |
| 5,406,265 | 4/1995 | Trozzo et al. | 340/632 |
| 5,442,348 | 8/1995 | Mushell | 340/932.2 |
| 6,031,454 | 2/2000 | Lovejoy et al. | 340/539 |

*Primary Examiner*—Edward Lefkowitz
*Assistant Examiner*—Davetta W. Goins
*Attorney, Agent, or Firm*—Frishauf, Holtz, Goodman, Langer & Chick, P.C.

[57] ABSTRACT

Apparatus for monitoring pollution generated by motor vehicles in an urban area, said area being equipped with a plurality of items of street furniture, each of which is provided with data acquisition and processing means (11, 21) for acquiring and processing data, and with communication means (12, 22) for communicating the data to a central site (30). The monitoring apparatus includes at least one item of street furniture (10, 20) further provided with at least one detector (13, 23) for detecting a magnitude characteristic of pollution, and suitable for delivering a measurement of said magnitude to the data acquisition and processing means (11, 21).

6 Claims, 1 Drawing Sheet

DEVICE FOR MONITORING POLLUTION CAUSED BY MOTOR VEHICLES IN AN URBAN AREA

FIELD OF THE INVENTION

The present invention relates to apparatus for monitoring pollution generated by motor vehicles in an urban area.

BACKGROUND OF THE INVENTION

The invention can be applied particularly advantageously to detecting and preventing motor vehicle pollution in an urban environment, regardless of whether the pollution is due to the presence in ambient air of a chemical pollutant, of the exhaust gas type, or is due to the noise produced by the engines and the motion of the vehicles.

Today, the constant increase in motor vehicle traffic in the centers of large conurbations gives rise to atmospheric pollution which, for example, can in some cases reach a level such that it endangers peoples' health.

Already, certain local authorities have shown concern for this problem, and have attempted to install apparatus for monitoring air quality. Such apparatus is, in general, constituted by instrument cabinets provided with detectors and placed high up, and suitable for measuring the concentration of polluting gases that are to be encountered in an urban atmosphere. In addition to being very voluminous, complex, and costly, known monitoring apparatus suffers from the drawback that the number of installed items of such apparatus is very small, in the range 1 to 10 items of apparatus in any one town or city, and the geographical distribution of pollution cannot therefore be determined accurately. In addition, such apparatus measures pollution as a whole, regardless of its origin. In particular, especially because of the height at which the detectors are situated, it is not possible to determine the pollution actually suffered by the people in town, or the proportion of the pollution that is generated by motor vehicles. Finally, current monitoring apparatus merely records pollutant concentration measurements during the day so that they can be centrally processed at a later date, without it being possible to react in real time, within an acceptable time limit, when pollution peaks are reached.

SUMMARY OF THE INVENTION

The technical problem to be solved by the present invention is thus to provide apparatus for monitoring pollution generated by motor vehicles in an urban area, which apparatus makes it possible, in simple and low-cost manner, to establish accurately the distribution of motor vehicle pollution in the area in question, and to offer means for reacting in real time on motor vehicle traffic so as to reduce the pollution as quickly as possible when a determined threshold is exceeded.

According to the invention, the solution to the technical problem posed consists in that, with said area being equipped with a plurality of items of street furniture, each of which is provided with data acquisition and processing means for acquiring and processing data and with communications means for communicating said data to a central site, said monitoring apparatus includes at least one item of street furniture further provided with at least one detector for detecting a magnitude characteristic of pollution, and suitable for delivering a measurement of said magnitude to said data acquisition and processing means.

In particular, in an embodiment of the invention, said items of street furniture are pay-and-display parking meters.

Similarly, the invention makes provision for said magnitude characteristic of pollution to be constituted by the concentration of a chemical pollutant in ambient air and/or the sound level due to noise produced by said motor vehicles.

The monitoring apparatus of the invention offers numerous advantages. Firstly, it uses an already-existing infrastructure of street furniture, which means that the cost is relatively low, the cost being represented essentially by installing a pollutant detector and/or a sound transducer, and by adapting the data acquisition and treatment means merely by modifying software. In addition, items of street furniture, such as pay-and-display parking meters offer dense geographical coverage, making it possible to obtain accurate knowledge of pollution distribution, even if only one or two pay-and-display parking meters per street are equipped. Furthermore, pay-and-display parking meters, like most items of street furniture, are ideally placed heightwise to detect pollution in the places where it is felt most strongly, and to evaluate pollution predominantly of motor vehicle origin. Moreover, the fact that said items of street furniture are connected in a network to a central site makes it possible, without significant modification, to centralize the pollution measurements taken, the centralizing being performed by subsequent processing with a view to establishing exact mapping, street-by-street, of the pollution over one day or one week, all of this data being very useful to define a traffic plan that is better from the point of view of motor vehicle pollution.

The invention further makes provision for the data acquisition and processing means to comprise storage means for storing a plurality of sampled measurements of the magnitude characteristic of pollution, and computation means for computing parameters representative of said pollution. The item of street furniture in question can thus deliver, at regular time intervals, said representative parameters, such as sliding hourly averages, relative to official specifications.

Finally, according to another advantageous characteristic of the invention, the data acquisition and processing means are suitable for establishing an alarm message when at least one of said parameters representative of pollution exceeds a determined threshold. This threshold exceeded data is transmitted in real time to the authorities via the central site for information purposes and for possible decision-taking. It is also possible for the monitoring apparatus to react automatically when, according to the invention, said central site is provided with control means serving, in the event that said threshold is exceeded, to control street furniture for prevention purposes, the effect of which is to block access to certain streets or certain sectors by using traffic lights, signposts, retractable bollards, or moving barriers, or by informing motorists by means of signposts displaying variable messages, asking them to stop their vehicles, or even directing them to parking areas at which parking charges could be temporarily reduced.

BRIEF DESCRIPTION OF THE DRAWING

What the invention consists of and how it may be implemented will be well understood on reading the following description with reference to the accompanying drawing which is given by way of non-limiting example and in which.

DETAILED DESCRIPTION OF THE PREFERRED EMBODIMENT

Figure 1:
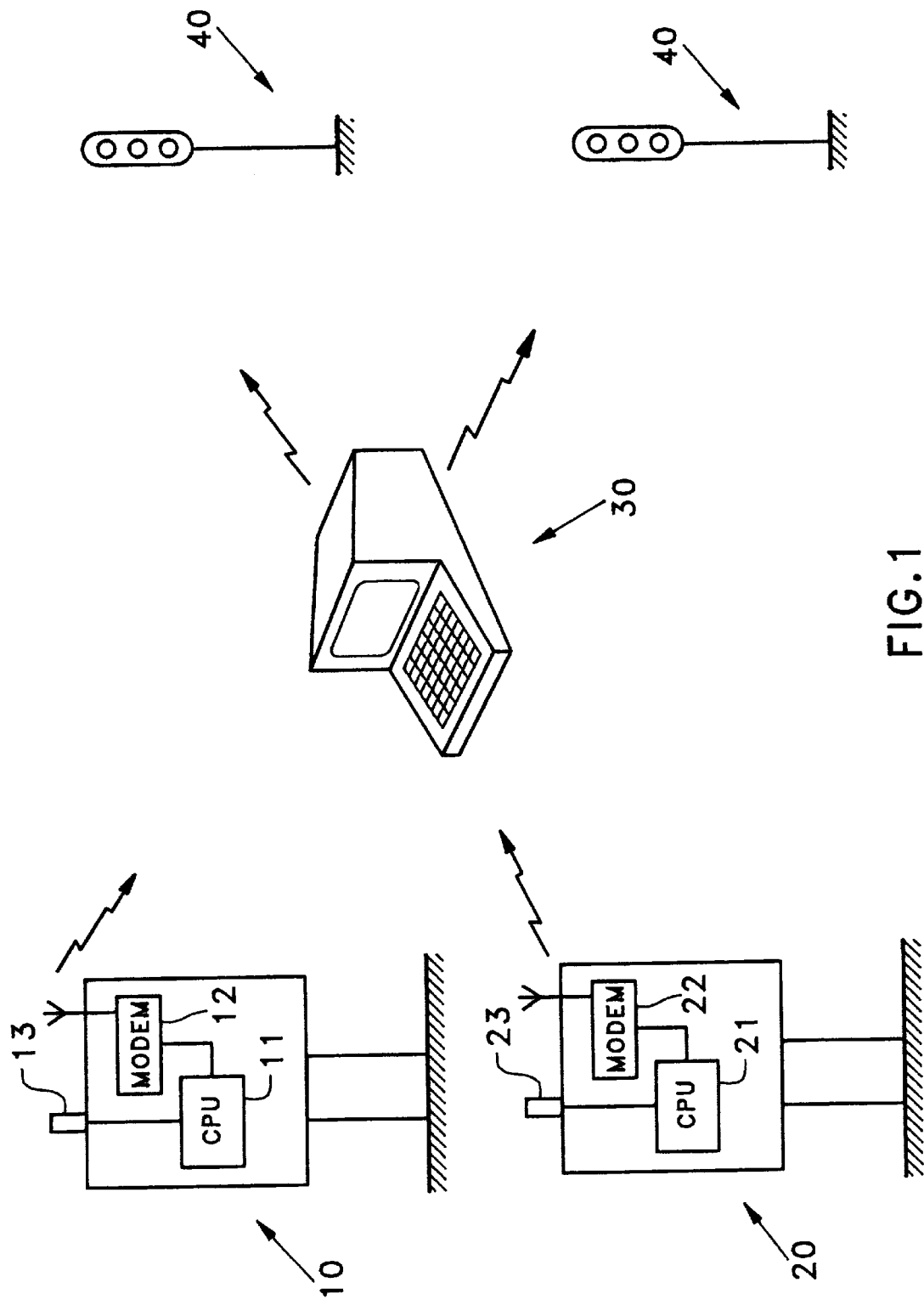
FIG. 1 is a diagram showing apparatus for monitoring pollution generated by motor vehicles in an urban area.

The apparatus includes items of street furniture, represented in this example by two pay-and-display parking meters 10, 20, situated in the urban area in which motor vehicle pollution is to be monitored.

The pay-and-display parking meters 10, 20 are originally equipped with data acquisition and processing means 11, 21 constituted by a central processing unit assigned to the task of managing the corresponding pay-and-display parking meter, as well as with communications means 12, 22 for communicating with a central site 30. In the embodiment shown in FIG. 1, the communications means are modems serving to set up radio links with said central site 30, it being possible for said radio links to be replaced with telephone links or some other type of link. The pay-and-display parking meters are provided with the central processing units 11, 21 in particular to detect operating anomalies such as breakdown of certain members or the end of ticket roll. This data is then directed to the central site 30 via the modems 12, 22 so that the maintenance department can act accordingly.

As shown in FIG. 1, the pay-and-display parking meters 10, 20 are also provided with detectors 13, 23 for detecting a chemical pollutant that is characteristic of motor vehicle pollution, e.g. carbon monoxide CO. In known manner, the corresponding detectors may be infrared, electrochemical, or electrical sensors suitable for measuring variations in the conductivity of a chip of $SiO_2$. Naturally, it is quite possible to choose other motor vehicle pollutants, such as nitrogen oxides NO, $NO_2$, etc.

It is to be understood that the reference made herein to chemical pollution only is in no way limiting, and that the invention also extends to noise pollution caused by motor vehicle traffic, the pay-and-display parking meters 10 and 20 then being equipped, optionally in association with the detectors 13, 23, with sound transducers, such as microphones, whose relation to the other members of the pay-and-display parking meters is entirely identical to that described below with reference to the chemical pollution detectors 13, 23.

The detectors 13, 23 are connected to the central processing units 11, 21 so as to transmit continuously thereto the measured value of the concentration of said pollutant in the ambient air, which concentration is the magnitude characteristic of pollution of chemical origin. As a result, said central processing units are organized to receive the measurements coming from the detectors 13, 23 in storage means, of the database type, in which said measurements are written at a given sampling rate, e.g. once every minute. These sampled measurements are transmitted to the central site 30 to be processed subsequently, in order, in particular, to establish accurate mapping of the motor vehicle pollution in the area in question, the pay-and-display parking meters 10, 20 being placed in appropriately chosen places. As mentioned above, this type of data can enable the authorities to define traffic plans offering lower pollution.

In addition to such subsequent processing aimed at long-term management of motor vehicle pollution, the monitoring apparatus of the invention offers the possibility of reacting in real time when pollution peaks are reached. For this purpose, in addition to said storage means, the central processing units 11, 21 include means for computing parameters representative of pollution, in compliance with the official specifications. By way of example, the parameter computed by said central processing units may be a sliding average over a given period (fifteen minutes or one hour) of the pollutant concentration measurements taken every minute.

The representative parameters are compared continuously with predetermined thresholds so that, in the event that the thresholds are exceeded, an alarm message is established intended for the central site 30. Since each pay-and-display parking meter 10, 20 is individually identified at said central site, it is always possible to know the geographical origin of the alarm, and thus to take suitable preventive measures. For this purpose, the central site 30 has control means, such as a radio link, for example, serving, when an alarm is received, to implement items of street furniture 40 in order to regulate motor vehicle traffic in the sector in which the pollution peak has been detected. The items of street furniture in question may be constituted by traffic lights, as shown in FIG. 1, but they may also be constituted by barriers, retractable bollards or signposts recommending that motorists stop their vehicles, if necessary in carparks whose charges have optionally been modified.

We claim:

1. Monitoring apparatus for monitoring pollution generated by motor vehicles in an urban area, said apparatus being characterized in that, with said area being equipped with a plurality of items of street furniture, each of which is provided with data acquisition and processing means (11, 21) for acquiring and processing data, and with communications means (12, 22) for communicating said data to a central site (30), said monitoring apparatus includes at least one item of street furniture (10, 20) further provided with at least one detector (13, 23) for detecting a magnitude characteristic of pollution, and suitable for delivering a measurement of said magnitude to said data acquisition and processing means (11, 21).

2. Monitoring apparatus according to claim 1, characterized in that the data acquisition and processing means (11, 21) comprise storage means for storing a plurality of sampled measurements of the magnitude characteristic of pollution, and computation means for computing parameters representative of said pollution.

3. Monitoring apparatus according to claim 2, characterized in that the data acquisition and processing means (11, 21) are suitable for establishing an alarm message when at least one of said parameters representative of pollution exceeds a determined threshold.

4. Monitoring apparatus according to claim 3, characterized in that said central site (30) is provided with control means serving, in the event that said threshold is exceeded, to control street furniture for prevention purposes (40).

5. Monitoring apparatus according to claim 1, characterized in that said items of street furniture are pay-and-display parking meters (10, 20).

6. Monitoring apparatus according to claim 1, characterized in that said magnitude characteristic of pollution is constituted by the concentration of a chemical pollutant in ambient air and/or the sound level due to noise produced by said motor vehicles.

* * * * *